United States Patent [19]

Shephard et al.

[11] 4,246,020

[45] Jan. 20, 1981

[54] IMIDAZOLE AND TRIAZOLE COMPOUNDS, FUNGICIDAL AND PLANT GROWTH REGULATING COMPOSITIONS, METHOD OF COMBATING FUNGAL INFECTIONS IN PLANTS AND METHOD OF REGULATING PLANT GROWTH

[75] Inventors: Margaret C. Shephard; Paul A. Worthington; Keith P. Parry, all of Maidenhead, England

[73] Assignee: Imperial Chemical Industries Limited, London, England

[21] Appl. No.: 964,728

[22] Filed: Nov. 29, 1978

[30] Foreign Application Priority Data

Dec. 7, 1977 [GB] United Kingdom ............... 50936/77
Nov. 3, 1978 [GB] United Kingdom ............... 43153/78

[51] Int. Cl.³ .................... A01N 43/50; A01N 43/64; C07D 233/60; C07D 249/08
[52] U.S. Cl. ........................... 71/76; 71/92; 542/429; 542/440; 542/470; 548/101; 548/262; 548/341; 424/245; 424/269; 424/273 R; 568/393; 568/412

[58] Field of Search ............... 542/429, 440, 470; 260/299, 308 R; 548/341, 101, 262; 424/269, 273, 245; 71/76, 92

[56] References Cited

U.S. PATENT DOCUMENTS

| 4,079,143 | 3/1978 | Balasubramanyan et al. ...... 542/429 |
| 4,086,351 | 4/1978 | Balasubramanyan et al. ...... 542/429 |
| 4,130,409 | 12/1978 | Shephard et al. .................... 424/269 |

*Primary Examiner*—Alton D. Hollins
*Attorney, Agent, or Firm*—Cushman, Darby & Cushman

[57] ABSTRACT

Compounds of formula

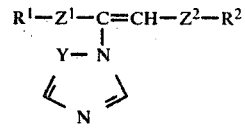

wherein Y is =N— or =CH—, $R^1$ and $R^2$ are alkyl, cycloalkyl, or phenyl and $Z^1$ and $Z^2$ are carbonyl or a derivative thereof, or salts or metal complexes thereof. These compounds have fungicidal and plant growth regulating activity.

7 Claims, No Drawings

IMIDAZOLE AND TRIAZOLE COMPOUNDS, FUNGICIDAL AND PLANT GROWTH REGULATING COMPOSITIONS, METHOD OF COMBATING FUNGAL INFECTIONS IN PLANTS AND METHOD OF REGULATING PLANT GROWTH

This invention relates to triazole and imidazole compounds useful as fungicides and plant growth regulating agents, to a process for preparing them, to fungicidal and plant growth regulating compositions containing them, to a method of combating fungal infections in plants using them and to a method of regulating the growth of plants using them.

The triazole and imidazole compounds have the general formula (I)

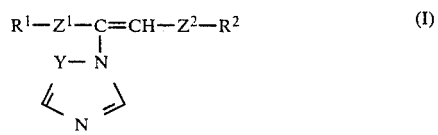

wherein Y is =N— or =CH—, each of $R^1$ and $R^2$, which may be the same or different, is unsubstituted or alkyl-substituted cycloalkyl (e.g. cyclopentyl, cyclohexyl or methylcyclohexyl), unsubstituted or halo-substituted alkyl (e.g. trichloromethyl) or unsubstituted or halo-, alkyl-, alkoxy-, phenyl- or nitro-substituted phenyl, and each of $Z^1$ and $Z^2$, which may be the same or different, is C=O or a derivative thereof (e.g. an imine, oxime, ketal, hydrazone or semicarbazone); or an acid addition salt or metal complex thereof.

The compounds of the invention contain chiral centres. The compounds are generally obtained in the form of racemic mixtures. However, these and other mixtures can be separated into the individual isomers by methods known in the art. The compounds also form geometrical isomers; mixtures of these isomers can be separated by methods known in the art.

The alkyl and alkoxy groups can be straight or branched chain groups having 1 to 6, e.g. 1 to 4 carbon atoms; examples are methyl, ethyl, propyl (n- or iso-propyl), butyl (n-, sec-, iso- or t-butyl), methoxy and ethoxy. The halogen atoms can be fluorine, chlorine, bromine, or iodine. Examples of the substituted phenyl groups are o-, m- or p-chlorophenyl, 2,4- or 2,6-dichlorophenyl, o-, m- or p-fluorophenyl, o-, m- or p-bromophenyl, o-, m- or p-methoxyphenyl, 2,4-dimethoxyphenyl, o-, m- or p-ethoxyphenyl, o-, m- or p-nitrophenyl, o-, m- or p-methylphenyl and p-phenylphenyl (p-biphenylyl). Suitably the phenyl group is unsubstituted or is substituted with 1, 2 or 3 substituents as defined above.

The salts can be salts with inorganic or organic acids e.g. hydrochloric, nitric, sulphuric, acetic, p-toluenesulfphonic or oxalic acid.

Suitably the metal complex is one including, as the metal, copper, zinc, manganese or iron. It preferably has the general formula:

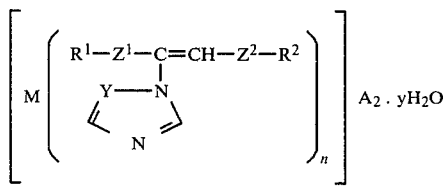

wherein Y, $R^1$, $R^2$, $Z^1$ and $Z^2$ are as defined above, M is a metal, A is an anion (e.g. a chloride, bromide, iodide, nitrate, sulphate or phosphate anion), n is 2 or 4 and y is 0 or an integer of 1 to 12.

Examples of the compounds of the invention are shown in Table I.

TABLE I

| COMPOUND NO | Y | $R^1$ | $R^2$ | $Z^1$ | $Z^2$ | MELTING POINT (°C.) |
|---|---|---|---|---|---|---|
| 1 | =N— | t-Bu | t-Bu | C=O | C=O | 107–108° |
| 2 | =N— | $C_6H_5$ | $C_6H_5$ | C=O | C=O | 130–132° |
| 3 | =N— | t-Bu | $C_6H_5$ | C=O | C=O | 95–97° |
| 4 | =N— | t-Bu | p-Cl—$C_6H_4$ | C=O | C=O | 140–141° |
| 5 | =N— | t-Bu | p-EtO—$C_6H_4$ | C=O | C=O | 134–135° |
| 6 | =N— | t-Bu | p-Br—$C_6H_4$ | C=O | C=O | 150–151° |
| 7 | =N— | t-Bu | p-$C_6H_5$—$C_6H_4$ | C=O | C=O | 139–140° |
| 8 | =N— | t-Bu | 2,4-di-MeO—$C_6H_3$ | C=O | C=O | 76–78° |
| 9 | =N— | t-Bu | p-F—$C_6H_4$ | C=O | C=O | 128–129° |
| 10 | =N— | t-Bu | p-Me—$C_6H_4$ | C=O | C=O | 136–137° |
| 11 | =N— | t-Bu | o-Cl—$C_6H_4$ | C=O | C=O | 69–70° |
| 12 | =N— | t-Bu | o-Me—$C_6H_4$ | C=O | C=O | gum |
| 13 | =N— | t-Bu | m-Me—$C_6H_4$ | C=O | C=O | 82–83° |
| 14 | =N— | t-Bu | m-$NO_2$—$C_6H_4$ | C=O | C=O | 153–154° |
| 15 | =N— | t-Bu | o-MeO—$C_6H_4$ | C=O | C=O | gum |
| 16 | =N— | t-Bu | p-MeO—$C_6H_4$ | C=O | C=O | 123–126° |
| 17 | =N— | p-Cl—$C_6H_4$ | t-Bu | C=O | C=O | gum |
| 18* | =N— | p-Cl—$C_6H_4$ | t-Bu | C=O | C=O | 148–150° |
| 19 | =N— | i-Pr | p-Cl—$C_6H_4$ | C=O | C=O | 128–129° |
| 20 | =N— | i-Pr | p-F—$C_6H_4$ | C=O | C=O | 90–91° |
| 21 | =N— | $C_6H_5$ | t-Bu | C=O | C=O | 97–9. |
| 22 | =N— | p-F—$C_6H_4$ | t-Bu | C=O | C=O | 45–47° |
| 23* | =N— | p-F—$C_6H_4$ | t-Bu | C=O | C=O | 116–118° |
| 24 | =N— | o-Me—$C_6H_4$ | t-Bu | C=O | C=O | oil |
| 25 | =N— | i-Pr | p-Me—$C_6H_4$ | C=O | C=O | 116–117° |
| 26 | =CH— | p-Cl—$C_6H_4$ | t-Bu | C=O | C=O | oil |
| 27 | =N— | 2,4-diCl—$C_6H_3$ | t-Bu | C=O | C=O | oil |
| 28 | =N— | 2,4-diCl—$C_6H_4$ | t-Bu | C=O | C=O | oil |
| 29 | =N— | i-Pr | p-MeO—$C_6H_4$ | C=O | C=O | 80–85° |
| 30 | =N— | i-Pr | o-MeO—$C_6H_4$ | C=O | C=O | 119–120° |
| 31 | =N— | i-Pr | o-MeO—$C_6H_4$ | C=O | C=O | gum |
| 32 | =N— | i-Pr | t-Bu | C=O | C=O | 63–64° |
| 33 | =N— | i-Bu | t-Bu | C=O | C=O | oil |

TABLE I-continued

| COMPOUND NO | Y | $R^1$ | $R^2$ | $Z^1$ | $Z^2$ | MELTING POINT (°C.) |
|---|---|---|---|---|---|---|
| 34 | =N— | i-Bu | t-Bu | C=O | C=O | oil |

*In the form of a hydrochloride salt.

Compounds 3 and 26 of Table I are mixtures of the E- and Z-isomers. Compounds 33 and 34 are isomeric mixtures wherein the weight ratios of the E-isomer to the Z-isomer are 10:1 and 2:1, respectively. Compounds 28 and 30 are E-isomers and Compounds 27 and 31 are Z-isomers. All the other compounds are single isomers of uncertain configuration.

The compounds of the invention may be made by reacting imidazole or 1,2,4-triazole, or a salt thereof, with the appropriate dihalo-δ-diketone of general formula (II):

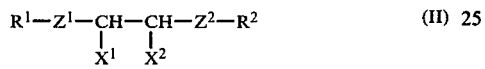

(II)

wherein $R^1$, $R^2$, $Z^1$ and $Z^2$ are are defined above, and each of the groups $X^1$ and $X^2$, which may be the same or different, is halogen (e.g. chlorine or bromine). This process is suitably carried out by heating the reactants together in a suitable solvent (such as acetonitrile, tetrahydrofuran or dimethylformamide); preferably it is performed by reacting the sodium salt of imidazole or 1,2,4-triazole with a dibromo-δ-diketone in for example boiling dimethylformamide. The product can be isolated by pouring the reaction mixture into water and recrystallizing the product from a convenient solvent.

The dihalo-δ-diketone starting material may be made by halogenation (e.g. bromination) of a compound of general formula (III):

(III)

wherein $R^1$, $R^2$, $Z^1$ and $Z^2$ are as defined above. Suitable brominating agents are bromine itself, N-bromosuccinimide and pyridinium hydrobromide perbromide.

The compound of general formula (III) may be made by methods set out in the literature.

The compounds of general formula (I) may also be made by reacting a compound of general formula (IV):

(IV)

wherein Y, $R^1$ and $Z^1$ are defined as above, with a compound of general formula (V):

(V)

where $R^2$ and $Z^2$ are defined as above, in the presence of a base (e.g. sodium methoxide or N-methylaniline magnesium bromide) to give a compound of general formula (VI):

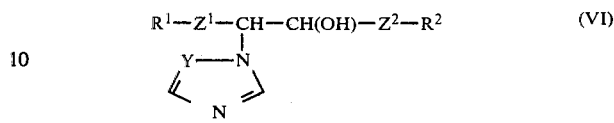

(VI)

wherein Y, $R^1$, $R^2$, $Z^1$ and $Z^2$ are as defined above. The compound of general formula (VI) can be dehydrated under standard conditions to give the compound of general formula (I). The dehydration is suitably achieved by using p-toluene sulphonyl chloride in pyridine.

The compounds of general formula (IV) and (V) may be made by methods set out in the literature.

The salts and metal complexes of the compounds of general formula (I) can be prepared from the latter in known manner. For example, the complexes can be made by reacting the uncomplexed compound with a metal salt in a suitable solvent.

The compounds, salts and metal complexes are active fungicides, particularly against the diseases:

*Piricularia oryzae* on rice

*Puccinia recondita, Puccinia striiformis* and other rusts on wheat, *Puccinia hordei, Puccinia striiformis* and other rusts on barley, and rusts on other hosts e.g. coffee, apples, vegetables and ornamental plants

*Plasmopara viticola* on vines

*Erysiphe graminis* (powdery mildew) on barley and wheat and other powdery mildews on various hosts such as

*Sphaerotheca fuliginea* on cucurbits (e.g. cucumber),

*Podosphaera leucotricha* on apples and *Uncinula necator* on vines

Helminthosporium spp. on cerals

*Cercospora arachidicola* on peanuts and other Cercospora species on for example sugar beet, bananas and soya beans

*Botrytis cinerea* (grey mould) on tomatoes, strawberries, vines and other hosts

*Phytophthora infestans* (late blight) on tomatoes

*Venturia inaequalis* (scab) on apples

Some of the compounds have also shown a broad range of activities against fungi in vitro. They have activity against various post-harvest diseases on fruit (e.g. *Penicillium digatatum* and *italicum* on oranges and *Gloeosporium musarum* on bananas). Further some of the compounds are active as seed dressings against: Fusarium spp., Septoria spp., Tilletia spp. (i.e. bunt, a seed borne disease of wheat), Ustilago spp., Helminthosporium spp. on cereals, *Rhizoctonia solani* on cotton and *Corticium sasakii* on rice.

The compounds also have plant growth regulating activities.

The plant growth regulating effects of the compounds are manifested as for example a stunting or dwarfing effect on the vegetative growth of woody and herbaceous mono- and di-cotyledonous plants. Such stunting or dwarfing may be useful, for example, in peanuts, cereals and soya bean where reduction in stem growth may reduce the risk of lodging and may also permit increased amounts of fertiliser to be applied. The stunting of woody species is useful in controlling the growth of undergrowth under power lines etc. Compounds which induce stunting or dwarfing may also be useful in modifying the stem growth of sugar cane thereby increasing the concentration of sugar in the cane at harvest; in sugar cane, the flowering and ripening may be controllable by applying the compounds. Stunting of peanuts can assist in harvesting. Growth retardation of grasses can help maintenance of grass swards. Examples of suitable grasses are *Stenotaphrum secundatum* (St. Augustine grass), *Cynosurus cristatus*, *Lolium multiflorum* and *perenne*, *Agrostis tenuis*, *Cynodon dactylon* (Bermuda grass), *Dactylis glomerata*, *Festuca* spp. (e.g. *Festuca rubra*) and *Poa* spp. (e.g. *Poa pratense*). The compounds may stunt grasses without significant phytotoxic effects and without deleteriously affecting the appearance (particularly the colour) of the grass; this makes such compounds attractive for use on ornamental lawns and on grass verges. They may also have an effect on flower head emergence in for example grasses. The compounds can also stunt weed species present in the grasses; examples of such weed species are sedges (e.g. Cyperus spp.) and dicotyledonous weeds (e.g. daisy, plantain, knotweed, speedwell, thistle, docks and ragwort). The growth of non-crop vegetation (e.g. weeds or cover vegetation) can be retarded thus assisting in the maintenance of plantation and field crops. In fruit orchards, particularly orchards subject to soil erosion, the presence of grass cover is important. However excessive grass growth requires substantial maintenance. The compounds of the invention could be useful in this situation as they could restrict growth without killing the plants which would lead to soil erosion; at the same time the degree of competition for nutrients and water by the grass would be reduced and this could result in an increased yield of fruit. In some cases, one grass species may be stunted more than another grass species; this selectivity could be useful for example for improving the quality of a sward by preferential suppression of the growth of undesirable species.

The dwarfing may also be useful in miniaturizing ornamental, household, garden and nursery plants (e.g. poinsettias, chrysanthemums, carnations, tulips and daffodils).

As indicated above, the compounds can also be used to stunt woody species. This property can be used to control hedgerows or to shape fruit trees (e.g. apples). Some coniferous trees are not significantly stunted by the compounds so the compounds could be useful in controlling undesirable vegetation in conifer nurseries.

The plant growth regulating effect may (as implied above) manifest itself in an increase in crop yield.

In the potato, vine control in the field and inhibition of sprouting in the store may be possible.

Other plant growth regulating effects caused by the compounds include alteration of leaf angle and promotion of tillering in monocotyledonous plants. The former effect may be useful for example in altering the leaf orientation of, for example, potato crops thereby letting more light into the crops and inducing an increase in phytosynthesis and tuber weight. By increasing tillering in monocotyledonous crops (e.g. rice), the number of flowering shoots per unit area may be increased thereby increasing the overall grain yield of such crops. In grass swards an increase in tillering could lead to a denser sward which may result in increased resilience in wear.

The treatment of plants with the compounds can lead to the leaves developing a darker green colour.

The compounds may inhibit, or at least delay, the flowering of sugar beet and thereby may increase sugar yield. They may also reduce the size of sugar beet without reducing significantly the sugar yield thereby enabling an increase in planting density to be made. Similarly in other root crops (e.g. turnip, swede, mangold, parsnip, beetroot, yam and cassava) it may be possible to increase the planting density.

The compounds could be useful in restricting the vegetative growth of cotton thereby leading to an increase in cotton yield.

The compounds may be useful in rendering plants resistant to stress since the compounds can delay the emergence of plants grown from seed, shorten stem height and delay flowering; these properties could be useful in preventing frost damage in countries where there is significant snow cover in the winter since then the treated plants would remain below the snow cover during the cold weather. Further the compounds may cause drought or cold resistance in certain plants.

When applied as seed treatments at low rates the compounds can have a growth stimulating effect on plants.

In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.1 to 15, preferably 0.1 to 5, kg per hectare is used. However, on certain plants even application rates within these ranges may give undesired phytotoxic effects. Routine tests may be necessary to determine the best rate of application of a specific compound for any specific purpose for which it is suitable.

The compounds may be used as such for fungicidal or plant growth regulating purposes but are more conveniently formulated into compositions for such usage. The invention thus provides also a fungicidal or plant growth regulating composition comprising a compound of general formula (I) or a salt or complex thereof as hereinbefore defined, and a carrier or diluent.

The invention also provides a method of combating fungal diseases in a plant, which method comprises applying to the plant, to seed of the plant or to the locus of the plant or seed a compound or salt or complex thereof as hereinbefore defined.

It also provides a method of regulating the growth of a plant, which method comprises applying to the plant, to seed of the plant or to the locus of the plant or seed a compound or salt or complex thereof as hereinbefore defined.

The compounds, salts and complexes can be applied in a number of ways, for example they can be formulated or unformulated, directly to the foliage of a plant, to seeds or to other medium in which plants are growing or are to be planted, or they can be sprayed on, dusted on or applied as a cream or paste formulation, or they can be applied as a vapour. Application can be to any part of the plant, bust or tree, for example to the foliage, stems, branches or roots, or to soil surrounding the roots, or to the seed before it is planted.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewett's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butoxyethanol).

The compositions to be used as sprays may also be in the form of aerosols wherein the formulation is held in a container under pressure in the presence of a propellant, e.g. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form.

By including suitable additives, for example additives for improving the distribution, adhesive power and resistance to rain on treated surfaces, the different compositions can be better adapted for various utilities.

The compounds can be used as mixtures with fertilizers (e.g. nitrogen-, potassium- or phosphorus-containing fertilizers). Compositions comprising only granules of fertilizer incorporating, for example coated with, the compound, are preferred. Such granules suitably contain up to 25% by weight of the compound. The invention therefore also provides a fertilizer composition comprising the compound of general formula (I) or a salt or metal complex thereof.

The compositions may also be in the form of liquid preparations for use as dips or sprays which are generally aqueous dispersions or emulsions containing the active ingredient in the presence of one or more surfactants e.g. wetting agent(s), dispersing agent(s), emulsifying agent(s) or suspending agent(s). These agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient(s). These concentrates suitably contain organic acids (e.g. alkaryl or aryl sulphonic acids such as xylenesulphonic acid or dodecylbenzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, e.g. compounds having similar or complementary fungicidal or plant growth regulating activity or compounds having herbicidal or insecticidal activity.

The other fungicidal compound can be for example one which is capable of combating ear diseases of cereals (e.g. wheat) such as Septoria, Gibberella and Helminthosporium spp., seed and soil borne diseases and downy and powdery mildews on grapes and powdery mildew and scab on apple etc. These mixtures of fungicides can have a broader spectrum of activity than the compound of general formula (I) alone; further the other fungicide can have a synergistic effect on the fungicidal activity of the compound of general formula (I). Examples of the other fungicidal compound are imazalil, benomyl, carbendazim (BCM), thiophanate-methyl, captafol, captan, sulphur, dithiocarbamates, carbathiins, copper oxychloride, triforine, dodemorph, tridemorph, dithianon, pyrazophos, binapacryl, quinomethionate, panoctine, furalaxyl, aluminium tris(ethylphosphonate), DPX3217, ethirimol, dimethirimol, bupirimate, chlorothalonil and metaxanine.

The compounds of general formula (I) can be mixed with soil, peat or other rooting media for the protection of plants against seed-borne, soil-borne of foliar fungal diseases.

Suitable insecticides are pirimor, croneton, dimethoate, metasystox and formothion.

The other plant growth regulating compound can be one which controls weeds or seedhead formation, improves the level or longevity of the plant growth regulating activity of the compounds of general formula (I), selectively controls the growth of the less desirable plants (e.g. grasses) or causes the compound of general formula (I) to act faster or slower as a plant growth regulating agent. Some of these other agents will be herbicides. Examples of suitable agents are the gibberellins (e.g. $GA_3$, $GA_4$ or $GA_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or BAP), phenoxyacetic acids (e.g. 2,4-D or MCPA), substituted benzoic acids (e.g. TIBA), morphactins (e.g. chlorfluorecol), maleic hydrazide, glyphosate, glyphosine, long chain fatty alcohols and acids (e.g. Off Shoot O or OFF Shoot T), dikegulac, Sustar, Embark, substituted quaternary ammonium and phosphonium compounds (e.g. CCC or Phosfon-D), Ethrel, carbetamide, Racuza, Alar, asulam, abscissic acid, isopyrimol, RH531, hydroxybenzonitriles (e.g. bromoxynil), Avenge, Suffix or Lontrel.

Belgian Patent Specification No. 848615 discloses inter alia certain 1-alkyl or aralkyl-1,2,4-triazolium salts. The compounds of the present invention are believed to have superior plant growth regulating and plant fungicidal activity.

The following Examples illustrate the invention; the temperatures are given in degrees Centigrade (°C.).

EXAMPLE 1

4-(1,2,4-Triazol-1-yl)-2,2,7,7-tetramethyl-oct-4-en-3,6-dione

Stage 1

A stirred solution of 2,2,7,7-tetramethyl-oct-4-en-3,6-dione (0.1 mol; m.p. 107°-9°; prepared according to the method of Ramasseul and Rassat, Bull. Soc. Chim. Fr., 1963, 2214-2217) in diethyl ether (200 ml) was treated dropwise with bromine (0.1 mol) at room temperature. After the bromine colour had been discharged, the ether was removed in vacuo to give a white crystalline solid. Recrystallization from ethanol gave 2,2,7,7-tetramethyl-4,5-dibromo-octan-3,6-dione (90%), m.p. 110°-111°.

Stage 2

Sodium hydride (100, %%, 0.06 mol) was added to a suspension of triazole (0.06 mol) in dimethyl formamide (100 ml) and the solution stirred at 20° until effervescence ceased. 2,2,7,7-Tetramethyl-4,5,dibromo-octan-3,6-dione (0.03 mol) was added portionwise at 20° to the stirred solution. After refluxing for 2 hours, the solution was cooled and poured into water to give a crystalline solid. Recrystallization from petroleum ether (60°-80°) gave the title compound as a white crystalline solid, m.p. 107°-8°.

EXAMPLE 2

2-(1,2,4-Triazol-1-yl)-1-phenyl-5,5-dimethyl-hex-2-en-1,4-dione

Stage 1 t-Butyl glyoxal (3.2 g; 0.03 mol) in tetrahydrofuran (THF; 5 ml) was added dropwise to a solution of N-methylaniline magnesium bromide (0.03 mol) in THF (40 ml) at 0° to give a deep red solution. p-Chlorophenacyl triazole (5.5 g, 0.025 mol) was added portionwise to give a white precipitate. After stirring for 15 minutes at 0°, the white solid was filtered off as 2-(1,2,4-triazol-1-yl)-1-phenyl-5,5-dimethylhexan-1,4-dione-3-ol. (4.1 g, 49%), m.p. 174°-5°.

Stage 2

The product (4.9 g, 0.015 mol) of Stage 1 and p-toluenesulphonyl chloride (3.0 g, 0.06 mol) were mixed together in pyridine (50 ml) at 20°. After standing at room temperature for 48 hrs, the solution was poured into crushed ice (50 ml)/concentrated hydrochloric acid (50 ml). The mixture was extracted with diethyl ether (100 ml), and the extract washed with water (3×100 ml) and dried over anhydrous sodium sulphate. Removal of the ether gave a brown gum which was further purified by column chromatography (silica gel eluted with diethyl ether) to give the title compound as a gum (2.8 g; 60%).

EXAMPLE 3

3-(1,2,4-Triazol-1-yl)-1-(p-chlorophenyl)-5,5-dimethyl-hex-2-en-1,4-dione

Stage 1

A solution of 3,3-dimethyl-1-(1,2,4-triazol-1-yl) butan-2-one (10 g) and 4'-chlorophenylglyoxal (11 g) in methanol (100 ml) was treated dropwise with 10% sodium-methoxide in methanol until a yellow colour began to develop. The solution was then stirred until a solid was precipitated. The whole reaction mixture then become solid and was filtered with suction. The solid was washed with methanol and air dried to give 1-(p-chlorophenyl)-5,5-dimethyl-3-(1,2,4-triazol-1-yl)hexan-1,4-dion-3-ol (16.7 g; 83%), m.p. 207°-209° (with decomposition).

Stage 2

A suspension of the product (16.7 g) of Stage 1 in pyridine (100 ml) was treated with p-toluene sulphonyl chloride (11 g) and shaken vigorously. The mixture was allowed to stand for 8 days with occasional shaking, during which time the solid dissolved and a dark red solution was obtained. The solution was then quenched with 2 N-hydrochloric acid (500 ml) and the resultant solid filtered off, washed with water and dried. Crystallization from petroleum ether gave the title product (15.4 g; 97%), m.p. 140°-140.5°.

EXAMPLE 4

The compounds were tested against a variety of foliar fungal diseases of plants. The technique employed was as follows.

The plants were grown in John Innes Potting Compost (No. 1, or Seed, as appropriate) in 4 cm diameter minipots. A layer of fine sand was placed at the bottom of the pot to facilitate uptake of test compound by the roots.

The test compounds were formulated either by bead-milling with aqueous Dispersol T or as a solution in acetone/ethanol which was diluted to the required concentration immediately before use. For the foliage diseases, 100 p.p.m. a.i. suspensions were sprayed on to the foliage and applied to the roots of the same plant via the soil. (Sprays were applied to maximum retention, and root drenches to a final concentration equivalent to approximately 40 ppm a.i./dry soil). Tween 20, to give a final concentration of 0.1%, was added when the sprays were applied to the cereals.

For most of the tests, the test compound was applied to the soil (roots) and to the foliage (by spraying) one or two days before the plant was inoculated with the diseases. An exception was the test on *Erysiphe graminis*, in which the plants were inoculated 24 hours before treatment. After inoculation, the plants were put into an appropriate environment to allow infection to take place and then incubated until the disease was ready for assessment. The period between inoculation and assessment varied from 4 to 14 days according to the disease and environment.

The disease control was recorded by the following grading:
4 = No disease
3 = 0-5%
2 = 6-25%
1 = 26-60%
0 = >60%

The results are shown in Table II wherein the symbol "–" indicates that the compound was not tested on the disease in question.

EXAMPLE 5

This Example illustrates the plant growth regulating properties of the compounds. The compounds were applied in the form of a 4000 p.p.m. solution in distilled water and the solution was then applied to the foliage of young seedlings of various plants. The experiments were replicated twice. After 21 days from treatment, the plants were assessed for plant growth regulating effects and phytotoxic symptoms.

Table III shows the stunting effect of the compounds on the vegetative growth using the following grading:
1 = 0-30% retardation
2 = 31-75% retardation
3 = >75% retardation Additional plant growth regulating properties are indicated as follows:
G = darker green leaf colour
A = apical effect
T = tillering effect The figure "0" indicates that the compound was substantially inactive as a plant growth regulating agent.

The symbol "–" indicates that the compound was not tested on that particular crop.

TABLE II

| COMPOUND NUMBER | PUCCINIA RECONDITA (Wheat) | ERYSIPHE GRAMINIS (Barley) | PIRICULARIA ORYZAE (Rice) | CERCOSPORA ARACHIDICOLA (Peanut) | PLASMOPARA VITICOLA (Vine) | PHYTOPHTHORA INFESTANS (Tomato) | BOTRYTIS CINEREA (Tomato) |
|---|---|---|---|---|---|---|---|
| 1  | 0 | 3 | 1 | — | 0 | 0 | 0 |
| 2  | 0 | 4 | 0 | — | 3 | 2 | 1 |
| 3  | 0 | 3 | 2 | 1 | 0 | 1 | 1 |
| 4  | — | — | 0 | — | 3 | 1 | 2 |
| 5  | — | — | 0 | — | 0 | 0 | 0 |
| 6  | — | — | 0 | — | 3 | 2 | 3 |
| 7  | 3 | 2 | 0 | — | 4 | 1 | 1 |
| 8  | 0 | 3 | 1 | 0 | 3 | 1 | 3 |
| 9  | 3 | 4 | 0 | — | 0 | 2 | 1 |
| 10 | 2 | 0 | 0 | — | 1 | 1 | 2 |
| 11 | 2 | 3 | 2 | — | 3 | 2 | 4 |
| 12 | 0 | 3 | 3 | — | 0 | 0 | 0 |
| 13 | 3 | 2 | 0 | — | 4 | 0 | 4 |
| 14 | 3 | 3 | 2 | — | 1 | 0 | 0 |
| 15 | 2 | 4 | 0 | — | 3 | 0 | 4 |
| 16 | 3 | 3 | 2 | — | 0 | 0 | 0 |
| 17 | 4 | 4 | 1 | 4 | 3 | 1 | 1 |
| 18 | 3 | 4 | — | — | 3 | 0 | 3 |
| 19 | 2 | 4 | 1 | 0 | 3 | 2 | 2 |
| 20 | 0 | 4 | 3 | 3 | 3 | 3 | 1 |
| 21 | 3 | 4 | 3 | 4 | 3 | 0 | 3 |
| 22 | 4 | 4 | 0 | — | 0 | — | 2 |
| 23 | 3 | 4 | 3 | 4 | 0 | 1 | 0 |
| 24 | 1 | 4 | 1 | — | 3 | 3 | 2 |
| 25 | 0 | 4 | 0 | 1 | 3 | 3 | 0 |
| 26 | 3 | 4 | 0 | 0 | 3 | 2 | 1 |
| 27 | 2 | 4 | 0 | 3 | 0 | 0 | 1 |
| 28 | 2 | 3 | 2 | 4 | 0 | 3 | 2 |
| 29 | 0 | 4 | 0 | 0 | 4 | 0 | 2 |
| 30 | 0 | 4 | — | 0 | 0 | 1 | 0 |
| 31 | 0 | 4 | — | 0 | 3 | 1 | — |
| 32 | 3 | 4 | 0 | 4 | 0 | 1 | 0 |
| 33 | 3 | 4 | 3 | 3 | 0 | 0 | 1 |

TABLE III

| Compound | Soya | Cotton | Rape | Sugar Beet | Agrostis Tenuis | Cynosurus Cristatus | Dactylis Glomerata | Winter Wheat | Barley | Rice | Maize | French Bean |
|---|---|---|---|---|---|---|---|---|---|---|---|---|
| 4  | 2GA | A  | 1GA | 2  | 2 | 2 | 1 | 2G | 2T | 1 | 0 | 2GA |
| 5  | 0   | 0  | 0   | 0  | 1 | 1 | 1 | 0  | 0  | 0 | 0 | 0   |
| 6  | 2A  | 2  | 2A  | 2A | 1 | 1 | 1 | 1  | 1  | 0 | 0 | A   |
| 7  | 0   | 1A | 0   | 0  | 0 | 0 | 0 | 0  | 0  | 0 | 0 | 0   |
| 8  | A   | 0  | 0   | 2A | 0 | 0 | 0 | 1  | 0  | 0 | 1 | 0   |
| 9  | 2GA | 1A | 1GA | 0  | 2 | 0 | 0 | 0  | 0  | 0 | 0 | 2A  |
| 10 | 2GA | 2A | 1G  | 0  | 1 | 1 | 1 | 1  | 1  | 0 | 0 | 0   |
| 11 | 2A  | 1A | 0   | 2  | 0 | 0 | 1 | 0  | 0  | 0 | 0 | 2A  |
| 12 | 1GA | 0  | 2   | 0  | 0 | 0 | 0 | 0  | 0  | 0 | 0 | 1A  |

TABLE III-continued

| Compound | Soya | Cotton | Rape | Sugar Beet | *Agrostis Tenuis* | *Cynosurus Cristatus* | *Dactylis Glomerata* | Winter Wheat | Barley | Rice | Maize | French Bean |
|---|---|---|---|---|---|---|---|---|---|---|---|---|
| 13 | 3GAT | 2A | 1 | 1G | 0 | 0 | 0 | 0 | 0 | 0 | 0 | 0 |
| 14 | 0 | 0 | 0 | 0 | 0 | 0 | 0 | 0 | 0 | 0 | 0 | 1A |
| 15 | 2AT | 0 | 0 | 2A | 0 | 0 | 0 | 0 | 0 | 0 | 0 | 0 |
| 16 | 0 | 0 | 0 | 2 | 0 | 0 | 0 | 0 | 0 | 0 | 0 | 0 |
| 19 | 1G | 0 | 0 | 0 | 3G | 3G | 3G | 2G | 0 | 0 | 0 | 1GA |
| 20 | 3GA | 3A | 0 | 0 | 3 | 3 | 3 | 0 | 0 | 0 | 0 | 2 |
| 24 | 1G | 0 | 2G | 2G | 0 | 0 | 0 | T | 1 | 0 | 0 | 3AT |
| 25 | 1 | 0 | 0 | 1 | 2 | 1 | 1 | 0 | 0 | 0 | 0 | 0 |
| 26 | 1 | 1 | 1 | 1G | 0 | 1 | 0 | 0 | 0 | 0 | 1 | 2A |
| 28 | 2G | 0 | 2 | 2G | 0 | 0 | 0 | 0 | 0 | 0 | 0 | 2A |
| 29 | 2GAT | 0 | 0 | 0 | 1 | 1G | 1 | 0 | 0 | 0 | 0 | 2AT |
| 30 | 0 | G | 0 | 0 | 0 | 0 | 0 | 0 | 0 | 0 | 0 | 2AT |
| 31 | G | 0 | 0 | G | 0 | 0 | 0 | 0 | 0 | 0 | 0 | 3AT |
| 32 | 1 | 2G | 0 | 1 | 0 | 1 | 0 | 0 | 0 | 0 | 0 | — |

We claim:

1. A compound of formula (I):

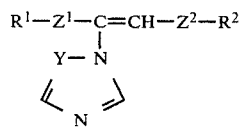

wherein Y is =N— or =CH—, each of $R^1$ and $R^2$, which may be the same of different, is $C_{3-6}$ cycloalkyl optionally substituted with one $C_{1-4}$ alkyl, $C_{1-4}$ alkyl optionally substituted with up to three halogens or phenyl optionally substituted with up to three substituents selected from the class consisting of halogen, nitro, phenyl, $C_{1-4}$ alkyl and $C_{1-4}$ alkoxy, and each of $Z^1$ and $Z^2$, which may be the same or different, is C=O or an acid addition salt or copper, zinc, manganese or iron complex thereof.

2. A compound as claimed in claim 1 wherein $R^1$ is propyl, butyl, phenyl, mono- or di-chlorophenyl, monofluorophenyl, or tolyl.

3. A compound as claimed in claim 2 wherein $R^1$ is i-propyl, i-butyl, t-butyl, phenyl, p-chlorophenyl, 2,4-dichlorophenyl, p-fluorophenyl or o-tolyl.

4. A compound as claimed in claim 1 wherein $R^2$ is butyl, phenyl, biphenylyl, monochlorophenyl, monofluorophenyl, monobromophenyl, tolyl, mono- or di-methoxyphenyl, monoethoxyphenyl or mononitrophenyl.

5. A compound as claimed in claim 4 wherein $R^2$ is t-butyl, phenyl, p-biphenylyl, o- or p-chlorophenyl, p-fluorophenyl, p-bromophenyl, o- or p-tolyl, o- or p-methoxyphenyl, 2,4-dimethoxyphenyl, p-ethoxyphenyl or m-nitrophenyl.

6. A fungicidal or plant growth regulating composition consisting essentially of, as active ingredient, a fungicidally or plant growth regulating effective amount of a compound, salt or complex as claimed in claim 1, and a carrier for the active ingredient.

7. A method of combating fungal diseases in, or regulating the growth of, a plant, the method consisting essentially of the step of applying to the plant, to seed of the plant or to the locus of the plant or seed, a fungicidally or plant growth regulating effective amount of a compound, salt or complex as claimed in claim 1.

* * * * *